United States Patent
Drinkwater et al.

(10) Patent No.: US 7,360,427 B2
(45) Date of Patent: Apr. 22, 2008

(54) COUPLING ELEMENT WITH VARYING WALL THICKNESS FOR AN ULTRASOUND PROBE

(75) Inventors: Bruce Walton Drinkwater, Ashton Gate (GB); Corin James Brotherhood, Chesterfield (GB)

(73) Assignee: The University of Bristol, Bristol (GB)

( * ) Notice: Subject to any disclaimer, the term of this patent is extended or adjusted under 35 U.S.C. 154(b) by 673 days.

(21) Appl. No.: 10/486,851

(22) PCT Filed: Sep. 8, 2003

(86) PCT No.: PCT/GB03/03891

§ 371 (c)(1),
(2), (4) Date: Feb. 13, 2004

(87) PCT Pub. No.: WO2004/025290

PCT Pub. Date: Mar. 25, 2004

(65) Prior Publication Data

US 2004/0254470 A1    Dec. 16, 2004

(30) Foreign Application Priority Data

Sep. 10, 2002  (GB) ................................. 0220986.4

(51) Int. Cl.
*G01N 29/14*  (2006.01)

(52) U.S. Cl. ........................... 73/635; 73/639; 73/641; 73/644

(58) Field of Classification Search ................ 73/635, 73/146, 637, 638, 639, 640, 641, 623, 625
See application file for complete search history.

(56) References Cited

U.S. PATENT DOCUMENTS

| | | | |
|---|---|---|---|
| 3,257,843 A | 6/1966 | Cowan | 73/71.5 |
| 4,098,132 A * | 7/1978 | Mikesell | 73/639 |
| 4,302,976 A | 12/1981 | Bull | 73/639 |
| 4,472,974 A | 9/1984 | Dickson et al. | 73/635 |
| 4,566,332 A * | 1/1986 | Collingwood | 73/639 |
| 4,640,133 A * | 2/1987 | Lecuru et al. | 73/639 |
| 5,434,827 A * | 7/1995 | Bolorforosh | 367/140 |

(Continued)

FOREIGN PATENT DOCUMENTS

DE   84 18 008.0   11/1985

(Continued)

OTHER PUBLICATIONS

International Search Report for PCT/GB03/03891 mailed Feb. 12, 2004.

(Continued)

*Primary Examiner*—Hezron Williams
*Assistant Examiner*—Jacques M. Saint-Surin
(74) *Attorney, Agent, or Firm*—Marshall, Gerstein & Borun LLP (57) ABSTRACT

An ultrasonic probe is provided in which an elongate array of transducers is disposed within an elongate coupling element which is mounted for rotation about an axle. The profile of the coupling element is chosen so as to provide a substantially uniform contact force with a surface over a predetermined area. To achieve this the radius of the coupling element varies along its length.

9 Claims, 6 Drawing Sheets

U.S. PATENT DOCUMENTS 5,641,909 A * 6/1997 Kiefer et al. .................. 73/623
5,763,800 A    6/1998 Rossum et al. ................ 84/603
5,864,056 A * 1/1999 Bell et al. ..................... 73/146

FOREIGN PATENT DOCUMENTS

| EP | 0 420 758   |   | 4/1991  |
| -- | ----------- | - | ------- |
| GB | 1118141     |   | 6/1968  |
| GB | 2044929     |   | 10/1980 |
| JP | 62-249056   |   | 10/1987 |
| JP | 11510917    |   | 9/1999  |
| JP | 2000296130 A | * | 10/2000 |

OTHER PUBLICATIONS

Great Britian Search Report for GB 0220986.4 dated Feb. 3, 2003.

* cited by examiner

COUPLING ELEMENT WITH VARYING WALL THICKNESS FOR AN ULTRASOUND PROBE

BACKGROUND

This patent relates to an ultrasound probe for non destructive investigation of materials and also to a coupling element for use with such a probe.

SUMMARY

Standard ultrasonic testing involves the coupling of an ultrasonic transducer to a test structure via a coupling medium which is commonly a liquid such as water or a coupling gel. In order to inspect a large structure the transducer is moved over the structure point by point, either manually or robotically, in order to build up an image of the structure. Manual scanning requires little specialist equipment but is quite time consuming. However the results are often subjective and no hard copy of the results are obtained. Automated scanning requires complex and expensive scanning systems but which typically generate hard copy of the results in the form of a defect map.

Structures almost inevitably have to be investigated in situ and hence manual inspection is often the only option as most automated scanning systems are not portable. Thus, in the context of an aircraft, it has to be inspected in its hanger or on the runway of an airport and this must be performed in parallel with other maintenance routines.

Boeing market a small automated scanning frame which can be secured to a large structure with rubber stickers. A scanner then scans the area within the frame in a raster fashion to build up a defect map. GB 2044929 discloses an alternative approach to hastening the speed of a manual scanning process. This document discloses an arrangement in which an ultrasonic transducer is housed within a fluid filled membrane which is itself formed into the shape of a tyre. The membrane is filled with thin oil at a pressure of approximately 2 lb. per square inch. The membrane is of uniform thickness, and in the example given in GB 2044929 the membrane forms a tyre having a diameter of 25 mm, and the membrane has a thickness of 0.635 mm. Such an arrangement probably works reasonably well with a very short or single ultrasonic probe. However, the same cannot be expected as the length of the probe, and hence the width of the swathe that the probe scans in a single pass, increases. The membrane has to remain fairly thin, and therefore suffers from tearing giving rise to a reduced in-service life before repair or replacement has to occur. In the case of "membrane tyre" systems such as that described in GB 2044929 the profiling of the membrane is not critical as the internal pressure sets the tyre shape and hence to a large approximation the membrane merely deforms to lie against the contacting surface.

According to a first aspect, there is provided an ultrasonic probe comprising a rotatable coupling element defining a transducer cavity and a plurality of ultrasonic transducers disposed within the transducer cavity, the coupling element being arranged, in use, to roll along a surface under investigation, wherein a thickness of the material forming a circumferential wall of the coupling element varies with position along the length of the coupling element, and the plurality of transducers forms an array extending along the longitudinal direction of the coupling element.

It is thus possible to provide a coupling element which may be thought of as a thick tyre, rather than as a membrane tyre of the prior art, which has a varying material depth within its outer wall, as opposed to a membrane of constant thickness as used in the prior art.

The use of such a "thick" tyre provides enhanced mechanical durability as the tyre no longer suffers from tearing. The tyre profile is also used in order to ensure that the correct contact characteristics is maintained along the working footprint of the tyre with the material under investigation.

Advantageously the wall of the tyre is at least 5 mm thick at its thickest point.

Preferably the profile of the tyre is chosen such that, in use, when the probe is placed against a surface under investigation and pressed against that surface with a force in excess of a predetermined minimum force, the coupling element deforms so as to produce a contact footprint greater than the beam size of the array formed by the plurality of ultrasonic transducers. Furthermore, for each transducer in the array the distance between the transducer and the inner surface of the coupling element, and the pressure acting between the coupling element and the surface under investigation is substantially uniform.

Preferably the coupling element is elongate along a longitudinal axis and the thickness of the circumferential wall of the coupling element increases with increasing distance from an end of the coupling element towards a midpoint of the coupling element.

Preferably the thickness of the circumferential wall of the coupling element varies in a smoothly changing manner.

The coupling element may be formed from a plurality of layers of material. This can facilitate the production of wide tyres. If a tyre is made from a single material, then as the tyre gets wider the thickness at its centre must be progressively increased otherwise tyre deformation may become excessive. Eventually this can cause problems since the attenuation of the ultrasound used to investigate the object under test increases with thickness of the material used to make the tyre. It would be possible to fabricate the coupling element using a harder material thereby allowing it to remain thin walled. This, in turn, makes it difficult to achieve good acoustic coupling to the item under test as higher contact pressures are needed to deform the tyre.

A preferred solution is to fabricate the tyre as a two piece element comprising a hard inner tyre and a soft outer tyre. In a preferred embodiment for a 100 mm wide tyre the inner tyre has a constant thickness of 6 mm and a Youngs modulus of 10 MPa, whereas the outer tyre has a thickness of 4 mm at the edges up to 6 mm at its centre and a Youngs modulus of 1 MPa.

The differing stiffnesses can be achieved by processing the same base monomer and varying the amounts of cross-linking agent added so as to achieve the differing stiffnesses. This is within the knowledge of the person skilled in the art.

Advantageously the coupling element is held on or between at least one, and preferably two, end elements. Where two end elements are provided they are located at either side of the coupling element and serve to define the ends of the transducer cavity. The end elements are advantageously in rotatable fluid sealed engagement with an axle of the ultrasonic probe. The axle engages with a carriage, yoke or handle in order to facilitate and control rolling motion of the coupling element over the surface under investigation. The transducers are advantageously fixed to the axle or to a support element which itself is fixed to the axle such that the orientation of the transducers is well defined.

The axle may be hollow, at least in part, so as to provide a pathway for electrical connections between the ultrasonic transducers and equipment for driving them and receiving returned signals.

Preferably the or each end element has a circularly symmetric rolling surface which, in use, abuts the surface under test once sufficient force has been applied to cause the required amount of deformation of the coupling element. Thus excess force above the predetermined minimum force does not cause further substantial deformation of the coupling element but instead is borne by the end elements.

Preferably the end elements have a peripheral layer of material having good frictional contact with the surface under inspection. Thus, the rolling force required to roll the probe along the surface under test is borne primarily by the end elements and consequently little or no shearing force occurs across the interface between the coupling element and the surface under inspection.

Preferably the ultrasonic array can be mounted at different positions within the transducer cavity. Thus one or both of the end elements and optionally the coupling element are arranged to be removable so as to facilitate adjustment of the ultrasonic transducers, or indeed substitution of ultrasonic transducers.

Because the plurality of ultrasonic transducers are arranged in an array having spatial extent along the longitudinal direction of the coupling element, the array of transducers can scan a swathe of the surface under investigation as the ultrasonic probe is moved across that surface.

Advantageously an internal groove having increased external diameter compared to the internal diameter of the coupling element is provided in one of the end elements such that any air within the transducer cavity can be trapped within the groove. Thus, prior to use, the probe can be orientated such that the groove is uppermost, thereby capturing the air. This is of benefit if the probe is to be used to scan the underside of an object.

Advantageously the yoke is arranged so as to hold the axle in a cantilever fashion thereby facilitating removal of one of the end elements and optionally the coupling element from the ultrasonic probe. The use of a cantilevered support also enables the probe to be brought into close abutment with upstanding walls.

Advantageously the transducers can be controlled so as to form a phased array such that the direction of look of the array can be electronically manipulated. The data from the transducers may then be processed electronically in order to form a defect map.

Advantageously the yoke further includes additional guide wheels of adjustable height to allow the orientation of the transducers with respect to the surface under investigation to be better defined. Advantageously the yoke includes a fluid spraying system, such as a water mist spraying system in order to enhance coupling between the coupling element and the surface under investigation.

The array of ultrasonic elements typically comprises between 8 and 128 elements, but these figures do not represent either minimum nor maximum limits.

According to a second aspect, there is provide a ultrasonic coupling element, the coupling element having a circumferential wall the thickness of which varies with longitudinal position along the coupling element.

The present invention will further be described, by way of example, with reference to the accompanying drawings, in which:

DETAILED DESCRIPTION

Figure 1:
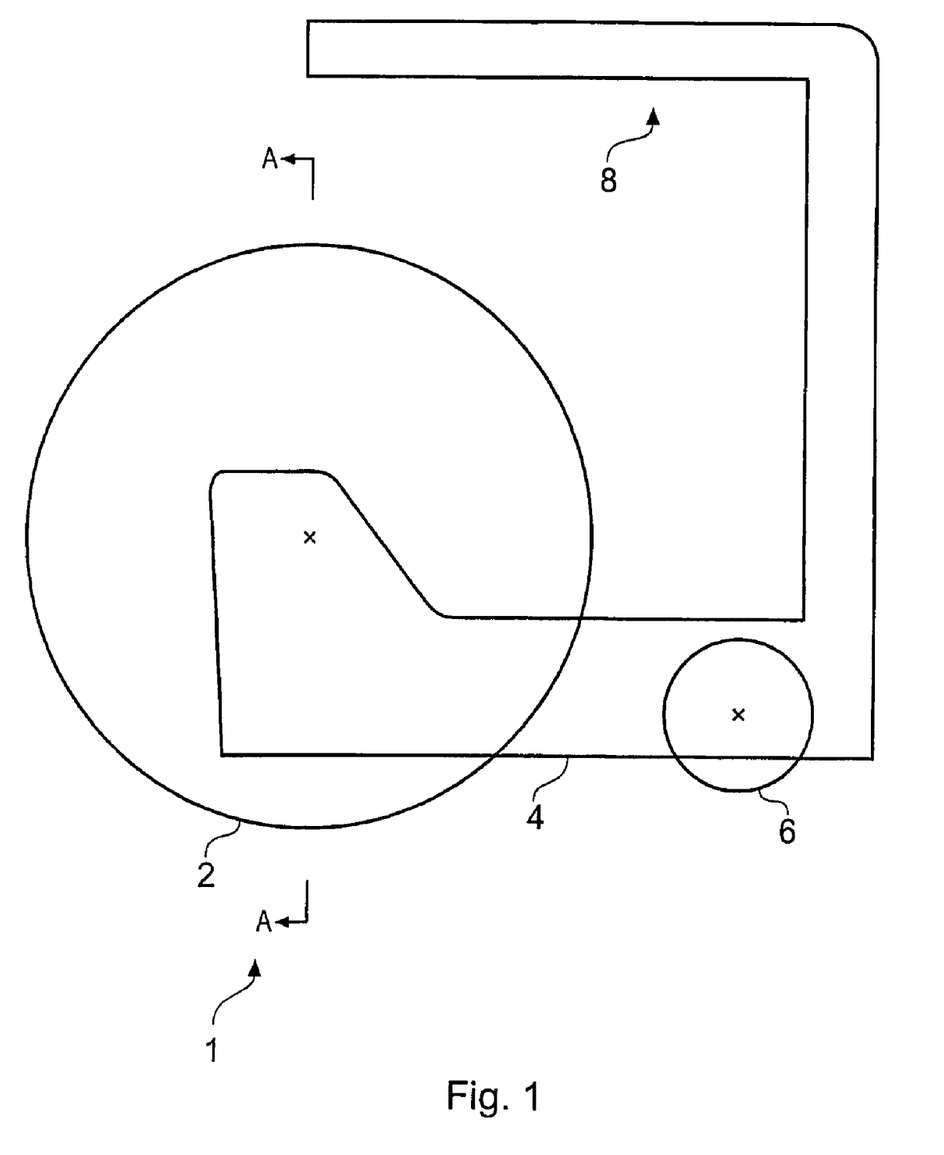
FIG. 1 is a schematic side view of a ultrasonic probe constituting an embodiment of the ultrasonic probe in accordance with the invention.

FIG. 1 schematically shows a ultrasonic probe, generally indicated 1, which can be moved along the surface of an item under inspection whilst performing a continuous investigation of that item. The probe comprises a probe assembly 2 which is rotatably mounted on a yoke 4. The yoke carries a wheel 6 which serves to make sure that the orientation of the ultrasonic probe is as intended by the designer (substantially perpendicular to the surface under test). The yoke 4 also carries a handle portion 8 which enables an operator to hold the probe 1 against an item under investigation and to move the probe over the surface of that item. Wheel 6 is also connected to a rotary encoder so as to determine probe position along a surface.

Figure 2:
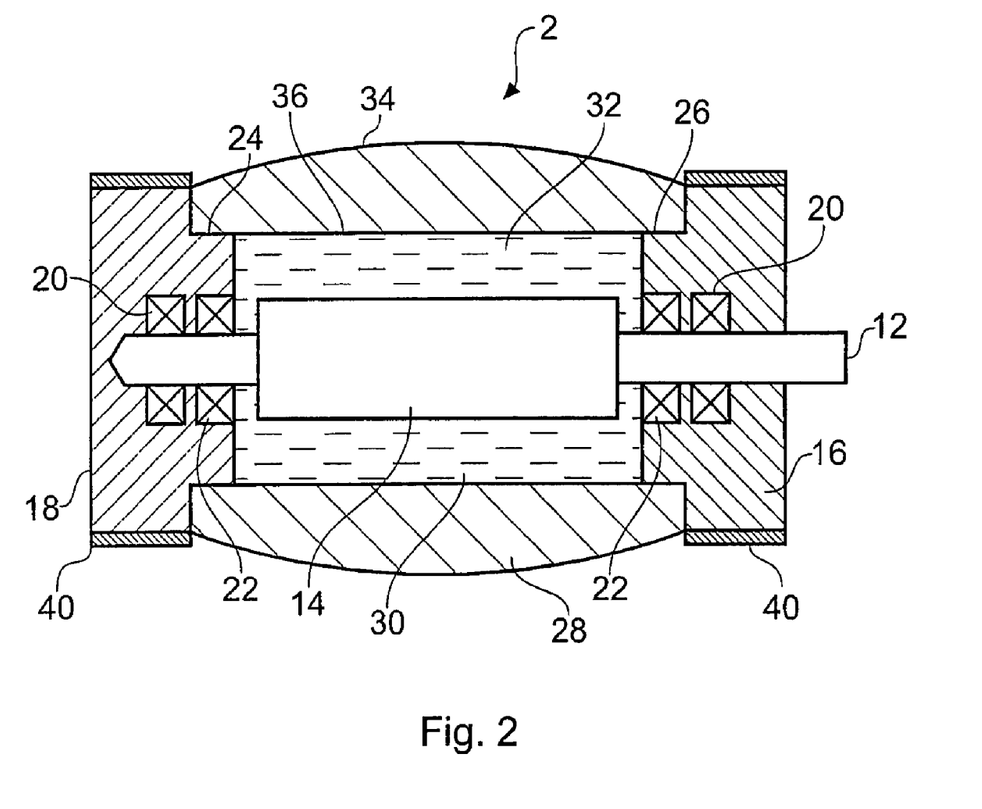
FIG. 2 is a cross section through the probe shown in FIG. 1 in the plane defined by the line A-A and the axle of the probe.

FIG. 2 schematically illustrates a configuration of the probe assembly 2 in greater detail. The assembly 2 comprises an axle 12 upon which an array of ultrasonic transducers 14 is mounted in such a configuration as to point towards the surface under investigation. The axle 12 also carries first and second end pieces, 16 and 18, respectively, which are rotatably mounted on the axle 12 by way of bearings 20. The end pieces 16 and 18 also include internal fluid tight seals 22 which sealingly engage around the axle 12. The first and second end pieces 16 and 18 have respective regions 24 and 26 of reduced circumference which face towards one another and which act as interface regions for supporting and engaging in a fluid sealed manner with a coupling element 28. The coupling element 28 together with the end elements 16 and 18 serves to define a transducer cavity 30 which is filled with a coupling liquid 32. As can be seen in FIG. 2, the depth of the material forming the coupling element 28, that is the depth of the material between an outer surface 34 and an inner surface 36 of the coupling element varies with axial displacement along the coupling element. In particular, the depth of the material in the coupling element is thinner in the regions towards the end elements 16 and 18 than in the central portion thereof.

The profile is selected, as will be described hereinafter, to ensure that the coupling element 28 forms a contact foot print with the surface under investigation, with the contact foot print being larger than an investigation aperture of the ultrasonic array. In this context, investigation aperture should be construed as meaning the effective area through which the ultrasonic energy is transmitted and received when investigating the item under test.

The end portions 16 and 18 have regions of high friction material 40 included thereon. The radius of the high friction material 40 is chosen to be slightly greater than the radius of the coupling element 28 at the intermediate interface with the end elements 16 and 18.

Figure 3:
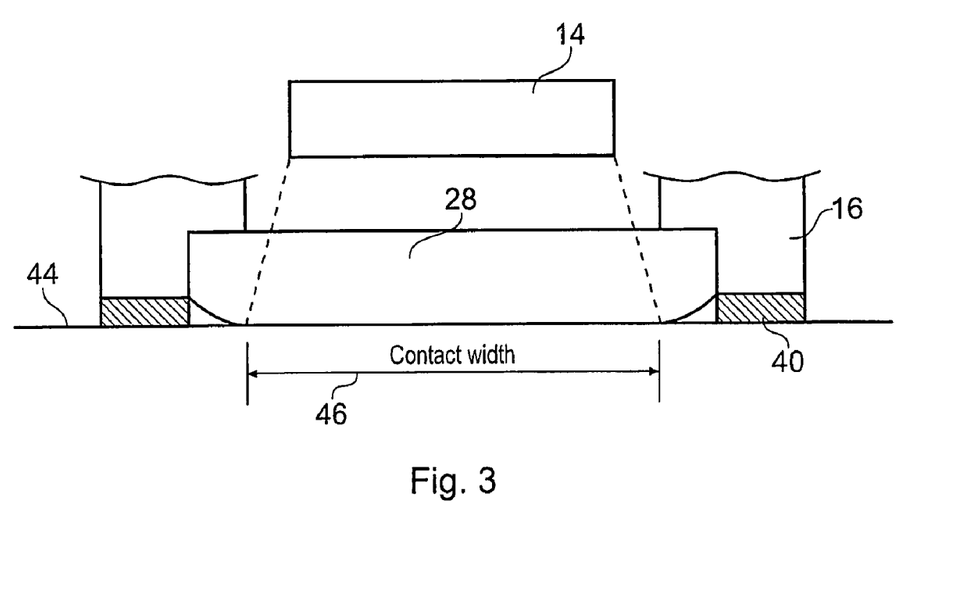
FIG. 3 shows the probe of FIG. 2 when in contact with a surface under investigation.

FIG. 3 shows the sensor arrangement of FIG. 2 in greater detail when pressed against a surface 44 under investigation.

Figure 4:
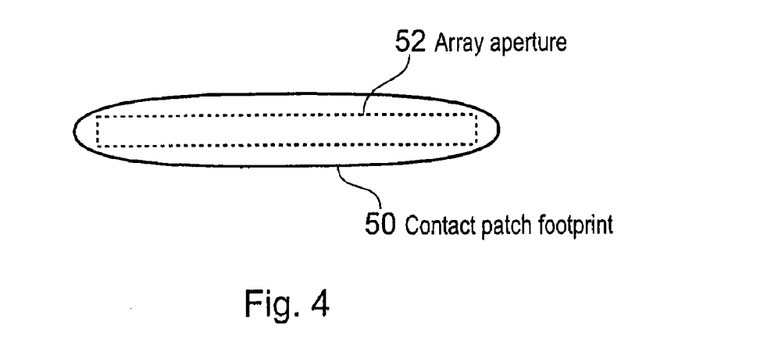
FIG. 4 schematically illustrates the contact foot print thereof.

As shown in FIG. 3, the coupling element 28 deforms such that its outer surface lies flat against the surface under investigation over a predetermined length 46. In fact, it will be appreciated that the area of contact extends both longitudinally as shown in FIG. 3 and laterally, as shown in FIG. 4 to define a contact foot print 50 which is selected so as to be larger than, and wholly contain, the array aperture 52.

Figure 5:
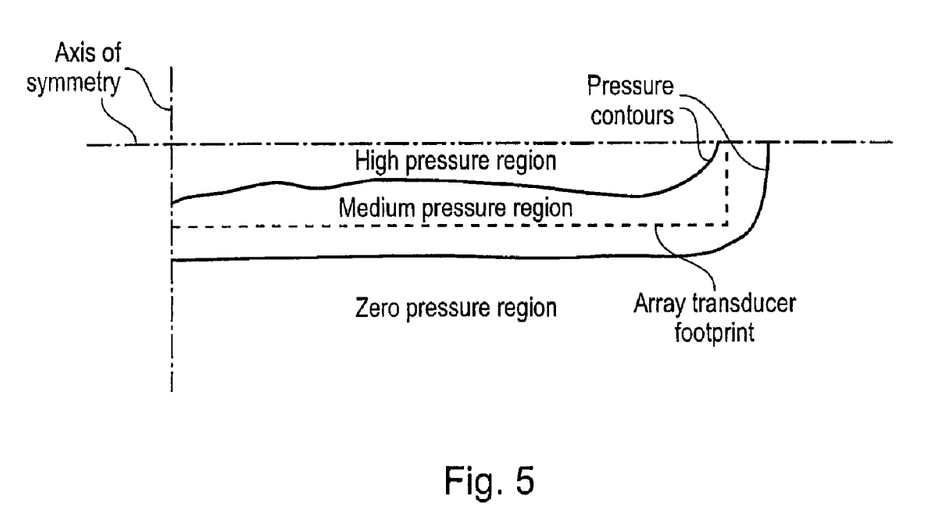
FIG. 5 schematically shows the contact pressure profile for the probe shown in FIG. 4.

It might initially be thought that the best shape of the coupling element 28 would be simply cylindrical, that is it would have a rectangular cross section. However this would result in extremely poor results as it generates an uneven contact pressure distribution with the higher pressures being generated towards the edges of the contact and the lowest pressure occurring towards the midpoint of the transducer array. Thus, in order to overcome this the depth of the element 28 needs to be profiled in order to make it thicker in the central section. However the requirement to have constant pressure all the way along means that this apparently simple task is non trivial. The inventor has used 3D finite element analysis to model the mechanical behaviours of the material making the coupling element at 28 in addition with the supporting forces provided by the end elements 16 and 18, the internal fluid pressure within the cavity 30 and the force supplied by the surface under test in order to achieve a suitable profile. FIG. 5 schematically illustrates the results of the computer modelling in terms of pressure regions acting within the material of the coupling element 28. It can be seen that the pressure can be divided into a high pressure region, and a medium pressure region within the material when it is in contact with the surface under investigation. The requirement is that the pressure contour at the interface with the surface under investigation should be substantially uniform.

Figure 6:
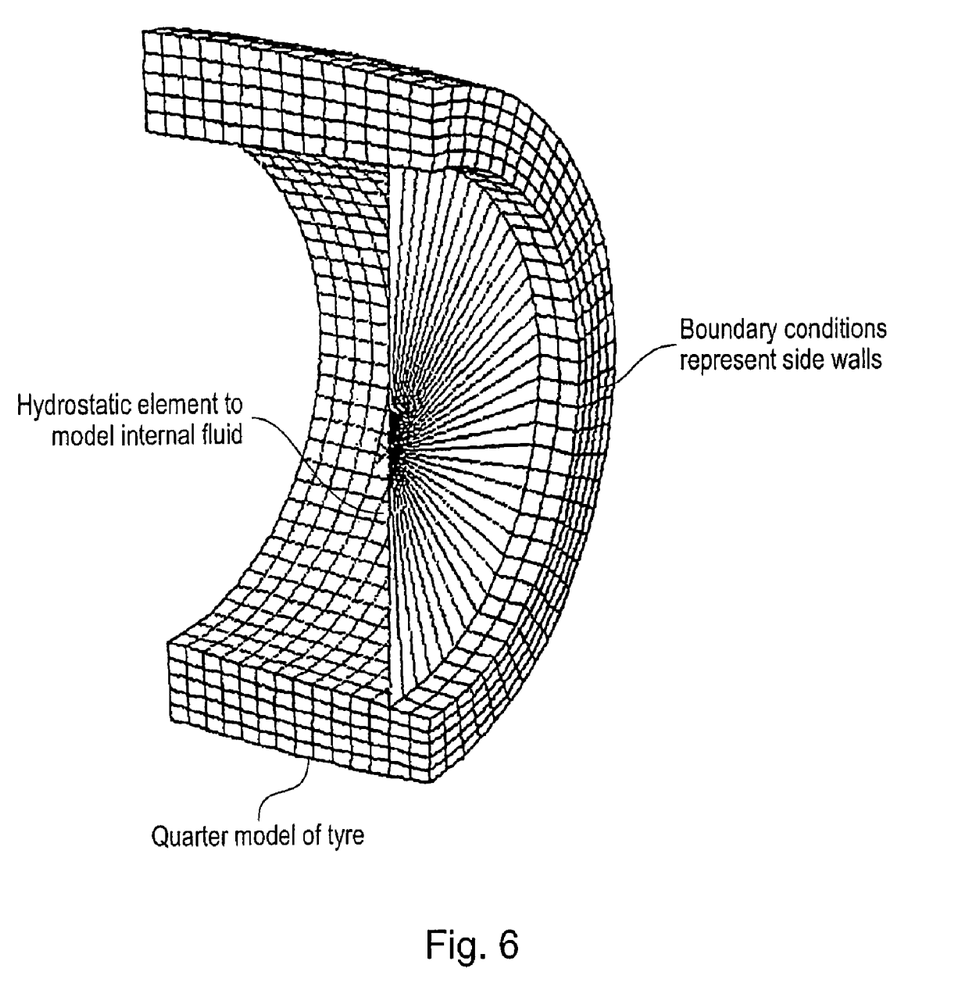
FIG. 6 schematically illustrates a finite element model of the tyre.

FIG. 6 schematically illustrates a finite element model of the coupling element 28.

Figure 7:
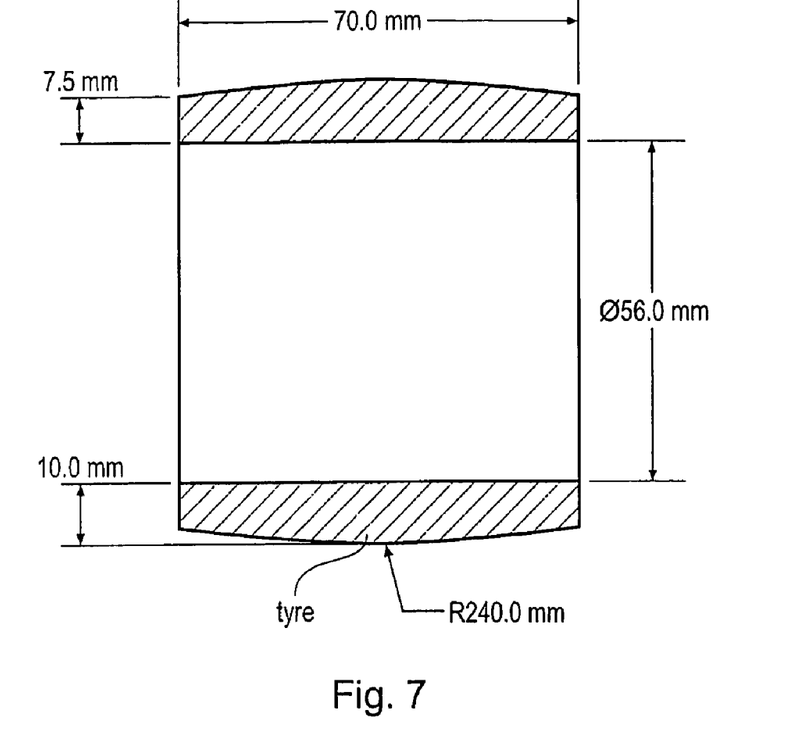
FIG. 7 is a representation of a tyre constituting an embodiment of the ultrasonic probe in accordance with the invention.

Through such numerical techniques, the inventor has derived a coupling element whose dimensions are shown in FIG. 7. In this example of the coupling element, the internal diameter of the element is 56 mm, the length of the element is 70 mm and the width of the wall of the element 28 ranges between 7.5 mm at the edges of the element to a maximum of 10 mm at the central region of the element. In this particular example the curvature of the outer surface of the element substantially corresponds to that of a circle having a radius of 240 mm. These parameters are dependent upon the material used to form the coupling element. The coupling element is typically formed of a elastomeric material, such as a soft rubber. The material chosen for the creation of the coupling element shown in FIG. 7 had a Youngs modulus of 1.3 MPa, a Poisson's ratio of substantially 0.49, a density of 957 Kgm$^{-3}$, and a longitudinal wave velocity of 1420 ms$^{-1}$. The density and longitudinal wave velocity was selected as they are similar to that of water which can be used as the fluid within the transducer cavity as it provides good ultrasonic coupling and has little environmental hazard.

The rubber ideally has low attenuation to ultrasound, and the rubber used had an attenuation of 10 MHz of approximately 143 Npm$^{-1}$. Suitable materials for the tyre include AN:VP, HEMA:MMA or polyamide:VP (VP is vinyl pyrrolidone, MMA is methyl methacrylate and AN is acrylonitrile).

The coupling element may be made of a plurality of coaxial layers to allow for greater tailoring of its mechanical properties. The layers may be of different thickness or hardness.

Figure 8:
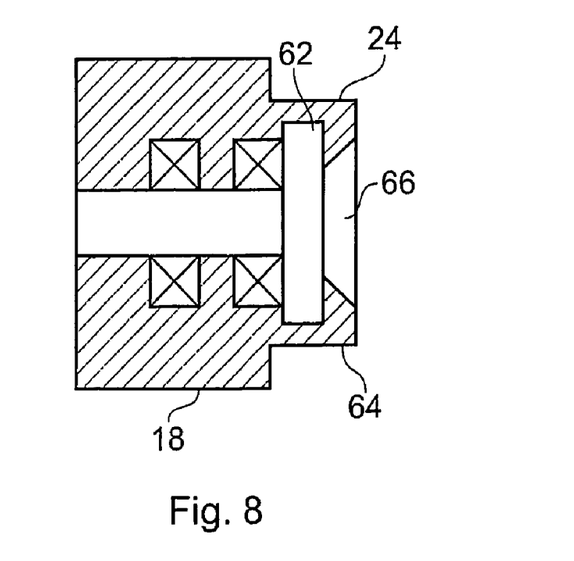
FIG. 8 shows a modification to an end piece.

FIG. 8 shows a modification to the end element 18 in which the end element 18 is machined to define a chamber 62 bounded by a wall 64 which defines an opening 66 of reduced radius. Thus if the probe is oriented with the opening facing downwardly, any air will enter into the chamber 62 and become trapped there when the probe is returned to its normal operating position.

It is thus possible to provide a coupling element in the form of a thick wall relatively elongate tyre which enables uniform contact pressure to be maintained over an elongate aperture for an elongate transducer array. The use of a longer array means that wider swathes of a surface can be inspected at a time and hence the inspection procedure is accomplished more quickly.

The invention claimed is:

1. An ultrasonic probe, comprising:
an elongate rotatable ultrasonic coupling element having a longitudinal axis defining a transducer cavity and having a plurality of ultrasonic transducers disposed within the transducer cavity,
the plurality of transducers forming an elongate array extending along the longitudinal direction of the coupling element, the coupling element having a circumferential wall thickness that varies with position along the length of the coupling element, wherein the ultrasonic probe comprises end elements with a circularly symmetric roiling surface and the coupling clement is disposed between the end elements that abut the surface of an object under investigation when a force in excess of a predetermined minimum force has been applied to bring the coupling element into contact with the object under investigation, said predetermined minimum force being sufficient to deform the coupling element to produce a longitudinally extending contact footprint greater than the elongate aperture of the elongate transducer array, said end elements are mounted for rotation with the coupling element and engage frictionally with the surface of the object under investigation such that the rolling force required to roll the probe along the surface under test is borne primarily by the end elements.

2. An ultrasonic probe as claimed in claim 1, in which the thickness of the circumferential wall of the coupling element is chosen with regard to the stiffness of the material used to form the coupling element to obtain a desired contact characteristic along a working footprint of the coupling element with the object under investigation.

3. An ultrasonic probe as claimed in claim 2, in which the working footprint of the coupling element is greater than the beam size of an ultrasonic beam produced by an array formed by the plurality of ultrasonic transducers.

4. An ultrasonic probe as claimed in claim 1, in which the coupling element is elongate along its longitudinal axis and the thickness of the circumferential wall increases with increasing distance from an end of the coupling element towards a midpoint of the coupling element.

5. An ultrasonic probe as claimed in claim 1, in which the coupling element is made from a plurality of layers of material such that the mechanical properties of each layer are individually adjustable.

6. An ultrasonic probe as claimed in claim 5, in which an inner layer of material is harder than an outer layer of material.

7. An ultrasonic probe as claimed in claim 1 in which an air trap is provided within the transducer cavity.

8. An ultrasonic probe as claimed in claim 7, in which the air trap comprises a groove of increased diameter compared to the internal diameter of the coupling element or of an aperture leading to the groove such that air can be trapped within the groove.

9. An ultrasonic probe as claimed in claim 1 in which the coupling element is held on a cantilevered support.

* * * * *

UNITED STATES PATENT AND TRADEMARK OFFICE
CERTIFICATE OF CORRECTION

PATENT NO.         : 7,360,427 B2                          Page 1 of 1
APPLICATION NO.    : 10/486851
DATED              : April 22, 2008
INVENTOR(S)        : Bruce W. Drinkwater et al.

It is certified that error appears in the above-identified patent and that said Letters Patent is hereby corrected as shown below:

On the Title Page:

Item (54), "COUPLING ELEMENT WITH VARYING THICKNESS FOR AN ULTRASOUND PROBE" should be -- ULTRASOUND PROBE --.

At Column 6, line 34, "roiling" should be -- rolling --.

Signed and Sealed this

Thirty-first Day of May, 2011

David J. Kappos
*Director of the United States Patent and Trademark Office*

UNITED STATES PATENT AND TRADEMARK OFFICE
CERTIFICATE OF CORRECTION

PATENT NO.         : 7,360,427 B2                                Page 1 of 1
APPLICATION NO.    : 10/486851
DATED              : April 22, 2008
INVENTOR(S)        : Bruce W. Drinkwater et al.

It is certified that error appears in the above-identified patent and that said Letters Patent is hereby corrected as shown below:

On the Title Page, Item (54) and at Column 1, lines 1-3, title:

"COUPLING ELEMENT WITH VARYING THICKNESS FOR AN ULTRASOUND PROBE" should be -- ULTRASOUND PROBE --.

At Column 6, line 34, "roiling" should be -- rolling --.

This certificate supersedes the Certificate of Correction issued May 31, 2011.

Signed and Sealed this
Twenty-eighth Day of June, 2011

David J. Kappos
*Director of the United States Patent and Trademark Office*